US011835610B2

(12) United States Patent
Rosen et al.

(10) Patent No.: US 11,835,610 B2
(45) Date of Patent: Dec. 5, 2023

(54) SYSTEMS AND METHODS FOR SUSCEPTIBILITY CONTRAST IMAGING OF NANOPARTICLES AT LOW MAGNETIC FIELDS

(71) Applicant: The General Hospital Corporation, Boston, MA (US)

(72) Inventors: Matthew S. Rosen, Somerville, MA (US); Zdenka Kuncic, Pennant Hills (AU); David Waddington, Erskineville (AU)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 17/866,069

(22) Filed: Jul. 15, 2022

(65) Prior Publication Data

US 2023/0029685 A1 Feb. 2, 2023

Related U.S. Application Data

(60) Provisional application No. 63/320,066, filed on Mar. 15, 2022, provisional application No. 63/222,927, filed on Jul. 16, 2021.

(51) Int. Cl.
| | |
|---|---|
| *G01R 33/561* | (2006.01) |
| *G01R 33/56* | (2006.01) |
| *G01R 33/44* | (2006.01) |
| *A61B 5/055* | (2006.01) |

(52) U.S. Cl.
CPC .......... *G01R 33/5614* (2013.01); *A61B 5/055* (2013.01); *G01R 33/445* (2013.01);
(Continued)

(58) Field of Classification Search
None
See application file for complete search history.

(56) References Cited

U.S. PATENT DOCUMENTS

| 7,573,268 B2 | 8/2009 | Volegov et al. |
| 8,519,705 B2 | 8/2013 | Savukov et al. |
| | (Continued) | |

FOREIGN PATENT DOCUMENTS

| WO | WO-2008035073 A2 * | 3/2008 | ............. G01N 24/08 |
| WO | 2014031985 A1 | 2/2014 | |
| | (Continued) | | |

OTHER PUBLICATIONS

Cunningham, et al., "Positive Contrast Magnetic Resonance Imaging of Cells Labeled with Magnetic Nanoparticles", Mag. Res. in Med., 53: 999-1005 (2005). (Year: 2005).*
(Continued)

*Primary Examiner* — Rodney E Fuller
(74) *Attorney, Agent, or Firm* — Quarles & Brady LLP (57) ABSTRACT

Systems and methods are provided for susceptibility contrast imaging of nanoparticles at low magnetic fields. A susceptibility-based MRI technique, such as imaging with a balanced steady-state free precession (bSSFP) pulse sequence, may be used for imaging a contrast agent such as biocompatible superparamagnetic nanoparticles at ultra-low fields. The contrast agent and imaging technique may be used to improving the visibility of anatomical structures and detecting diseases, such as cancer, with low-field MRI.

28 Claims, 5 Drawing Sheets

(52) U.S. Cl.
CPC ..... *G01R 33/5601* (2013.01); *G01R 33/5602* (2013.01); *G01R 33/5608* (2013.01)

(56) References Cited

U.S. PATENT DOCUMENTS

| | | | |
|---|---|---|---|
| 8,886,283 B1 | 11/2014 | Chen et al. | |
| 11,353,533 B2* | 6/2022 | Wang | A61B 5/055 |
| 2012/0003160 A1* | 1/2012 | Wolf | A61B 5/055 |
| | | | 424/9.3 |
| 2021/0338842 A1* | 11/2021 | Wu | A61K 49/0056 |

FOREIGN PATENT DOCUMENTS

| | | | |
|---|---|---|---|
| WO | 2018187825 A1 | 10/2018 | |
| WO | 2018187826 A1 | 10/2018 | |

OTHER PUBLICATIONS

Gharagouzloo, et al., "Quantitative Contrast-Enhanced MRI with Superparamagnetric Nanoparticles Using Ulrashort Time-to-Echo Pulse Sequences", Magn Reson Med. Aug. 2015; 74(2); 431-411. (Year: 2015).*

Mn, X., Russek, S.E., Zabow, G. et al. Large T1 contrast enhancement using superparamagnetic nanoparticles in ultra-low field MRI. Sci Rep 8, 11863 (2018). https://doi.org/10.1038/s41598-018-30264-5.

Sarracanie et al, Low-Cost High Performance MRI, Scientific Reports 5: Article 15177 (2015).

Vogel, M.W., Guridi, R.P., Su, J. et al. 3D-Spatial encoding with permanent magnets for ultra-low field magnetic resonance imaging. Sci Rep 9, 1522 (2019). https://doi.org/10.1038/s41598-018-37953-1.

* cited by examiner

SYSTEMS AND METHODS FOR SUSCEPTIBILITY CONTRAST IMAGING OF NANOPARTICLES AT LOW MAGNETIC FIELDS

CROSS-REFERENCE TO RELATED APPLICATIONS

This application claims the benefit of U.S. Provisional Patent Application Ser. No. 63/222,927 filed on Jul. 16, 2021 and entitled "Systems and Methods for Susceptibility Contrast Imaging of Nanoparticles at Low Magnetic Fields," and of U.S. Provisional Patent Application Ser. No. 63/320,066 filed on Mar. 15, 2022 and entitled "Systems and Methods for Susceptibility Contrast Imaging of Nanoparticles at Low Magnetic Fields," which are incorporated herein by reference as if set forth in their entirety for all purposes.

BACKGROUND

Magnetic resonance imaging ("MRI") is highly advantageous for noninvasive clinical imaging due to its high resolution, soft tissue contrast, and depth of penetration. Widely used for anatomical imaging, the physical basis of MRI is the detection of magnetic moments associated with spin-½ nuclei, such as hydrogen. When placed in a uniform static magnetic field (B0), these nuclear spins will precess about the static field with a characteristic frequency known as the Larmor frequency and will, on average, tend to align with the static field. If a substance containing these nuclear spins is subjected to a radiofrequency pulse (B1) at the Larmor frequency, the net alignment of the spins can be rotated relative to the static magnetic field, producing a net transverse magnetic moment. As the spins precess at the Larmor frequency, so too does the net transverse magnetic moment, generating an oscillatory magnetic field that can be inductively detected to give a magnetic resonance signal.

To acquire images with MRI, the magnetic resonance signals are usually measured multiple times with different combinations of magnetic field gradients applied. These magnetic field gradients vary the magnetic field over the sample of interest, causing spatial variations in the Larmor frequency. Knowledge of the spatial shift in the Larmor frequency enables images of nuclear spin distribution to be reconstructed from sets of MR signals.

MRI has been unparalleled in its ability to non-invasively image soft tissue since it was introduced to the clinic over 30 years ago. However, decades of technical improvements have not reduced the price of an MRI scanner which, mostly due to superconducting magnets and siting infrastructure requirements, is nominally $1M USD per Tesla of magnetic field. Such high costs have meant that MRI has typically been available only to relatively wealthy populations in areas of high population density.

Recently, the clear market for a low-cost, portable MRI scanner, particularly in the field of emergency medicine, has led to the design and construction of several prototype MRI scanners that operate at low magnetic fields (<~0.3 T), where it becomes economically advantageous to generate the main B0 magnetic field with permanent magnets. Further reduction of B0 into the ultra-low field regime (B0<10 mT), makes possible MRI scanners based on inexpensive, and lightweight, electromagnets. Utilizing modern hardware and new acquisition techniques, this new wave of low-cost scanners can acquire far superior diagnostic information to earlier generations of low-field MRI scanners and could become common screening tools, particularly at remote hospitals and medical clinics.

MRI scanners operating at ultra-low magnetic fields (ULF), such as <10 mT, are uniquely positioned to reduce the cost and expand the clinical accessibility of MRI. A fundamental challenge for ULF MRI is obtaining high contrast images without compromising acquisition sensitivity to the point that scan times become clinically unacceptable. Recently, MRI scanners operating at ultra-low magnetic fields have demonstrated clinically useful imaging of the brain. By lowering the B0 magnetic field from more than 1 T to substantially less than 10 mT, these ULF scanners enable MRI to be performed with electromagnets rather than bulky and costly cryogenic magnets. Such ULF MRI scanners are in commercial development stages at present, with an expected cost of $100k per scanner rather than the $2M+ of conventional MRI systems. It is expected that at this price point, ULF MRI scanners will become common screening tools at remote hospitals and medical clinics, whilst also buffering demand for higher resolution but much more expensive conventional MRI scanners in major hospitals.

The clinical applications of ULF MRI will be greatly determined by the availability of suitable contrast agents, which are currently lacking. Contrast agents are exogenous substances, administered either orally or by injection, that show up clearly in MRI images, improving the visibility of internal body structures as well as aiding in the detection of tumors and inflammation.

Conventional MRI contrast agents are typically small molecules that shorten what are known as the spin-lattice (T1) and spin-spin relaxation times (T2) of adjacent 1H nuclear spins. These T1 and T2 relaxation times characterize the time taken for the nuclear spins to align with the B0 field and the lifetime of the transverse magnetic moment. Changes in T1 and T2 affect the magnitude of the MR signal detected, thereby modulating the brightness of contrast agent containing regions in MRI scans.

Unfortunately, in ULF MRI, the weak alignment of nuclear spins with B0 demands the use of high efficiency acquisition sequences that are insensitive to changes in T1 and T2. Further, the intrinsic contrast between tissues is reduced in ULF MRI as T1 and T2 times of all substances tend to converge at low fields.

Susceptibility imaging, an MRI technique commonly used at conventional field strengths, generates contrast via local magnetization differences in the substance being imaged. These magnetization differences are described by variations in susceptibility (the property of a material that indicates whether it is attracted into or repelled out of a magnetic field) and are induced by the B0 magnetic field that the substance being imaged is placed in. Hence, susceptibility differences result in local changes in magnetic field strength and thus, changes in the Larmor frequency of the nuclear spins being imaged. With an appropriate imaging protocol, these frequency changes lead to MRI contrast around substances of different susceptibility. However, susceptibility imaging has not been demonstrated in ULF MRI to date because the magnetization changes induced in human tissue are over 100 times smaller in ULF MRI than in conventional MRI.

Conventional relaxivity techniques for generating contrast at conventional magnetic field strengths (more than 1T), modulate brightness with changes in T1 and T2 relaxation times. Due to the intrinsic low signal-to-noise ration of MRI at ULF, a prohibitive amount of signal averaging resulting in acquisition times in excess of an hour would be required to generate an image with conventional relaxivity at ULF. These times are far too long for an implementation in a clinical setting.

In some ULF MRI methods, Overhauser based techniques have been relied upon for imaging contrast agents, which rely upon the transfer of spin magnetization from free radicals to hydrogen nuclei on application of resonant radiofrequency (RF) drive fields. Such techniques are limited by short in vivo lifetimes of free radicals (they are rapidly reduced by anti-oxidants over a few minutes at most) and high RF powers required to drive the spin magnetization transfer process. Conventionally, the required RF powers for this are in excess of the safety limits for human use for these field strengths and are therefore not applicable for clinical use.

Given the imminent arrival of ULF MRI as a diagnostic tool, there is a clear need for suitable contrast agent imaging techniques. At present, no suitable ULF MRI contrast agent imaging technique exists for clinical use.

SUMMARY OF THE DISCLOSURE

The present disclosure addresses the aforementioned drawbacks by providing systems and methods for susceptibility contrast imaging of nanoparticles at using low field MRI (lf-MRI). A susceptibility-based MRI technique may be used for imaging a contrast agent such as biocompatible superparamagnetic nanoparticles at lf-MRI or ULF MRI. In a non-limiting example, the nanoparticles are superparamagnetic iron oxide nanoparticles (SPIONs). The contrast agent and imaging technique may be used to improving the visibility of anatomical structures and detecting diseases, such as cancer, with ULF MRI.

In one configuration, a low-field magnetic resonance imaging (lf-MRI) system is provided. The lf-MRI system includes at least one magnet configured to produce a low-field B0 magnetic field and at least one gradient coil system configured to produce magnetic fields to encode nuclear magnetic resonance signals emitted from the subject. The lf-MRI system also includes at least one radio-frequency (RF) coil system configured to produce excitation pulses. The lf-MRI system also includes and at least one computer system configured to: control the gradient coil system and the RF coil system to perform a balanced steady-state free precession (bSSFP) pulse sequence to acquire lf-MRI data from a subject having received a dose of superparamagnetic nanoparticles. The computer system is also configured to reconstruct an image of the subject having received a dose of superparamagnetic nanoparticles. The image may have a negative contrast induced by the spin-spin (R2) relaxivity of the superparamagnetic nanoparticles in the low-field B0 or a positive contrast created by susceptibility weighting of the lf-MRI data.

In one configuration, a method for magnetic resonance imaging is provided. Magnetic resonance data are acquired from a subject that has received a dose of superparamagnetic nanoparticles using an MRI system. Acquiring the magnetic resonance data includes controlling the MRI system to perform a balanced steady-state free precession (bSSFP) pulse sequence to acquire the magnetic resonance data from the subject. At least one parameter of the bSSFP pulse sequence is adjusted such that the magnetic resonance data contains one of a negative contrast for the superparamagnetic nanoparticles induced by the spin-spin relaxivity ($R_2$) of the superparamagnetic nanoparticles or a positive contrast for the superparamagnetic nanoparticles induced by susceptibility weighting. An image of the subject is reconstructed from the magnetic resonance data, where the image depicts the superparamagnetic nanoparticles with the negative contrast or the positive contrast based on the at least one parameter of the bSSFP pulse sequence.

It is another aspect of the present disclosure to provide a method for magnetic resonance imaging (MRI) of a subject that has been administered a dose of superparamagnetic nanoparticles. The method includes acquiring susceptibility-weighted magnetic resonance data from a subject that has received a dose of superparamagnetic nanoparticles using an MRI system performing a pulse sequence. An image of the subject is reconstructed from the susceptibility-weighted magnetic resonance data, where at least one of a radio frequency tip angle, a frequency offset, or a repetition time of the pulse sequence is selected such that the superparamagnetic nanoparticles are depicted in the image with a positive contrast.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention. Like reference numerals will be used to refer to like parts from Figure to Figure in the following description.

DETAILED DESCRIPTION

Systems and methods are provided for susceptibility contrast imaging of nanoparticles at low magnetic fields. A susceptibility-based magnetic resonance imaging ("MRI") technique, such as imaging with a balanced steady-state free precession ("bSSFP") pulse sequence, may be used for imaging a contrast agent such as biocompatible superparamagnetic nanoparticles at low and/or ultra-low magnetic fields. In a non-limiting example, the nanoparticles are superparamagnetic iron oxide nanoparticles ("SPIONs"). The contrast agent and imaging technique may be used to improving the visibility of anatomical structures and detecting diseases, such as cancer, with ULF MRI. In some configurations, susceptibility-based MRI imaging may be used for imaging a contrast agent containing biocompatible superparamagnetic nanoparticles, such as SPIONs, using low-field MRI ("lf-MRI") or ultra-low-field ("ULF") MRI.

As a non-limiting example, low-field MRI can include performing MRI using a polarizing B0 field having a magnetic field strength in the range of less than 1.5 T, such as in a range between 0.1 T to 1.0 T. Similarly, ultra-low-field MRI can include performing MRI using a polarizing B0 field having a magnetic field strength less than 0.1 T, such as at or below 10 mT, at or below 6.5 mT, or the like.

A challenge to the implementation of lf-MRI and ULF-MRI remains simultaneously achieving signal-to-noise ratios ("SNRs") adequate for imaging and contrast-to-noise ratios ("CNRs") sufficient for diagnostic differentiation between tissues within a short imaging time. The traditionally low SNR of conventional (i.e. inductively detected) ULF MRI may be improved significantly through the use of high-efficiency sequences, such as bSSFP, which can accommodate rapid signal averaging. Such sequences, where spins are dynamically refocused and repolarized while signal is still being acquired, have enabled diagnostically useful images of the human brain to be acquired at ULF in minutes. Unlike spin-echo-based techniques at ULF, relaxation contrast in bSSFP acquisitions is reduced due to signal intensity being weighted by the ratio of spin-spin and spin-lattice relaxation times (T2/T1), which converges to unity at ULF.

The systems and methods described in the present disclosure make use of biocompatible SPIONs, or other superparamagnetic nanoparticles, that demonstrate high magnetizations and relaxivities in the ULF regime. Advantageously, by combining high-efficiency bSSFP sequences with the unique magnetization and relaxation properties of these SPIONs, or other superparamagnetic nanoparticles, at ULF, high-sensitivity imaging of exogenous contrast agents is enabled. These magnetizations can be exploited to perform sensitive, susceptibility-based SPION, or other superparamagnetic nanoparticle, imaging at ULF. It is a technical advantage of these disclosed techniques that positive contrast can be generated by variations in the acquisition parameters. Given the biocompatibility of SPIONs, or other superparamagnetic nanoparticles, and the potential for ULF MRI to enable medical imaging in remote locations, these results can allow for new clinical applications of MRI, particularly in the field of emergency medicine.

Some embodiments described in the present disclosure implement susceptibility imaging in the low-field regime where ULF MRI scanners operate using SPIONS, or other superparamagnetic nanoparticles, of compositions and sizes that lead to them have unusually high magnetizations, even at very low magnetic fields. As a non-limiting example, a bSSFP imaging sequence, which is highly efficient, can be used to allow for rapid imaging even at ultra-low fields. Advantageously, the bSSFP imaging sequence can be adjusted to image susceptibility with positive contrast. Unlike negative contrast, which is the conventional method used for imaging SPIONs in high-field MRI, positive contrast enables the location of SPIONs in images to be seen as "bright" spots on a dark background. This "bright" detection removes ambiguity from the interpretation of images and aids in the clear diagnosis of medical conditions. The disclosed techniques have advantageous applications in ULF MRI, such as aiding in the diagnosis of tumors. Gadolinium-based contrast agents fulfill this role in conventional high-field MRI scanners, but do not give sufficient contrast in ULF MRI due to the suppression of T1 contrast with high efficiency sequences.

Figure 1:
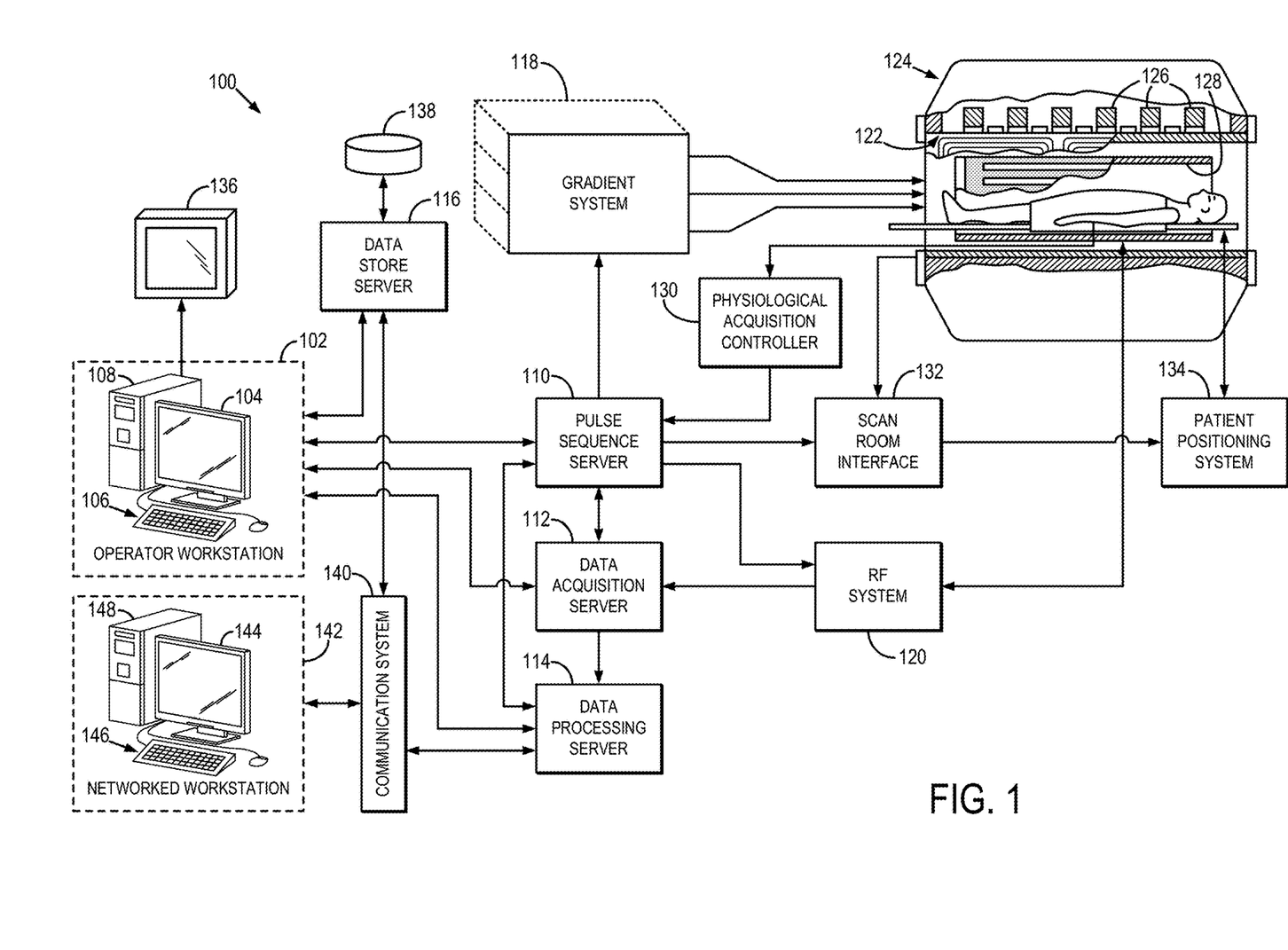
FIG. 1 is a block diagram of a non-limiting example of an MRI system that can implement the systems and methods in accordance with the present disclosure.

Referring particularly now to FIG. 1, an example of an MRI system 100 that can implement the methods described in the present disclosure is illustrated. In some configurations, the MRI system 100 is a low-field MRI system with a B0 magnetic field less than 1.0 T, which is less than the field strength of 1.5 T used in conventional MRI systems. For example, the B0 magnetic field can have a field strength of less than 1.0 T, which may include a field strength in a range between 0.1 T and 1.0 T, a field strength at or less than 0.3 T, a field strength at or less than 10 mT, and so on. In some embodiments, the B0 magnetic field can have a field strength of 6.5 mT, or less. In still other configurations, the MRI system 100 has a conventional field strength, such as a field strength grater than 1.0 T, which may include a field strength of 1.5 T, 3.0 T, and the like.

The MRI system 100 includes an operator workstation 102 that may include a display 104, one or more input devices 106 (e.g., a keyboard, a mouse), and a processor 108. The processor 108 may include a commercially available programmable machine running a commercially available operating system. The operator workstation 102 provides an operator interface that facilitates entering scan parameters into the MRI system 100. The operator workstation 102 may be coupled to different servers, including, for example, a pulse sequence server 110, a data acquisition server 112, a data processing server 114, and a data store server 116. The operator workstation 102 and the servers 110, 112, 114, and 116 may be connected via a communication system 140, which may include wired or wireless network connections.

The pulse sequence server 110 functions in response to instructions provided by the operator workstation 102 to operate a gradient system 118 and a radiofrequency ("RF") system 120. Gradient waveforms for performing a prescribed scan are produced and applied to the gradient system 118, which then excites gradient coils in an assembly 122 to produce the magnetic field gradients $G_x$, $G_y$, and $G_z$ that are used for spatially encoding magnetic resonance signals. The gradient coil assembly 122 forms part of a magnet assembly 124 that includes a polarizing magnet 126 and a whole-body RF coil 128. In some configurations, the polarizing magnet 126 may include a bi-planar electromagnet operating at a 6.5 mT magnetic field, and the gradient coil assembly 122 may include bi-planar magnetic gradients coils. Other magnet coil geometries and configurations can also be used.

RF waveforms are applied by the RF system 120 to the RF coil 128, or a separate local coil to perform the prescribed magnetic resonance pulse sequence. Responsive magnetic resonance signals detected by the RF coil 128, or a separate local coil, are received by the RF system 120. The responsive magnetic resonance signals may be amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the prescribed scan and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. An RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \quad (1);$$

and the phase of the received magnetic resonance signal may also be determined according to the following relationship:

$$\varphi = \tan^{-1}\left(\frac{Q}{I}\right). \quad (2)$$

The pulse sequence server 110 may receive patient data from a physiological acquisition controller 130. By way of example, the physiological acquisition controller 130 may receive signals from a number of different sensors connected to the patient, including electrocardiograph ("ECG") signals from electrodes, or respiratory signals from a respiratory bellows or other respiratory monitoring devices. These signals may be used by the pulse sequence server 110 to synchronize, or "gate," the performance of the scan with the subject's heart beat or respiration.

The pulse sequence server 110 may also connect to a scan room interface circuit 132 that receives signals from various sensors associated with the condition of the patient and the magnet system. Through the scan room interface circuit 132, a patient positioning system 134 can receive commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, so that data is not lost by data overrun. In some scans, the data acquisition server 112 passes the acquired magnetic resonance data to the data processor server 114. In scans that require information derived from acquired magnetic resonance data to control the further performance of the scan, the data acquisition server 112 may be programmed to produce such information and convey it to the pulse sequence server 110. For example, during pre-scans, magnetic resonance data may be acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also process magnetic resonance signals used to detect the arrival of a contrast agent in a magnetic resonance angiography ("MRA") scan. For example, the data acquisition server 112 may acquire magnetic resonance data and processes it in real-time to produce information that is used to control the scan.

The data processing server 114 receives magnetic resonance data from the data acquisition server 112 and processes the magnetic resonance data in accordance with instructions provided by the operator workstation 102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 114 are conveyed back to the operator workstation 102 for storage. Real-time images may be stored in a data base memory cache, from which they may be output to operator display 102 or a display 136. Batch mode images or selected real time images may be stored in a host database on disc storage 138. When such images have been reconstructed and transferred to storage, the data processing server 114 may notify the data store server 116 on the operator workstation 102. The operator workstation 102 may be used by an operator to archive the images, produce films, or send the images via a network to other facilities.

The MRI system 100 may also include one or more networked workstations 142. For example, a networked workstation 142 may include a display 144, one or more input devices 146 (e.g., a keyboard, a mouse), and a processor 148. The networked workstation 142 may be located within the same facility as the operator workstation 102, or in a different facility, such as a different healthcare institution or clinic.

The networked workstation 142 may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142.

Figure 2:
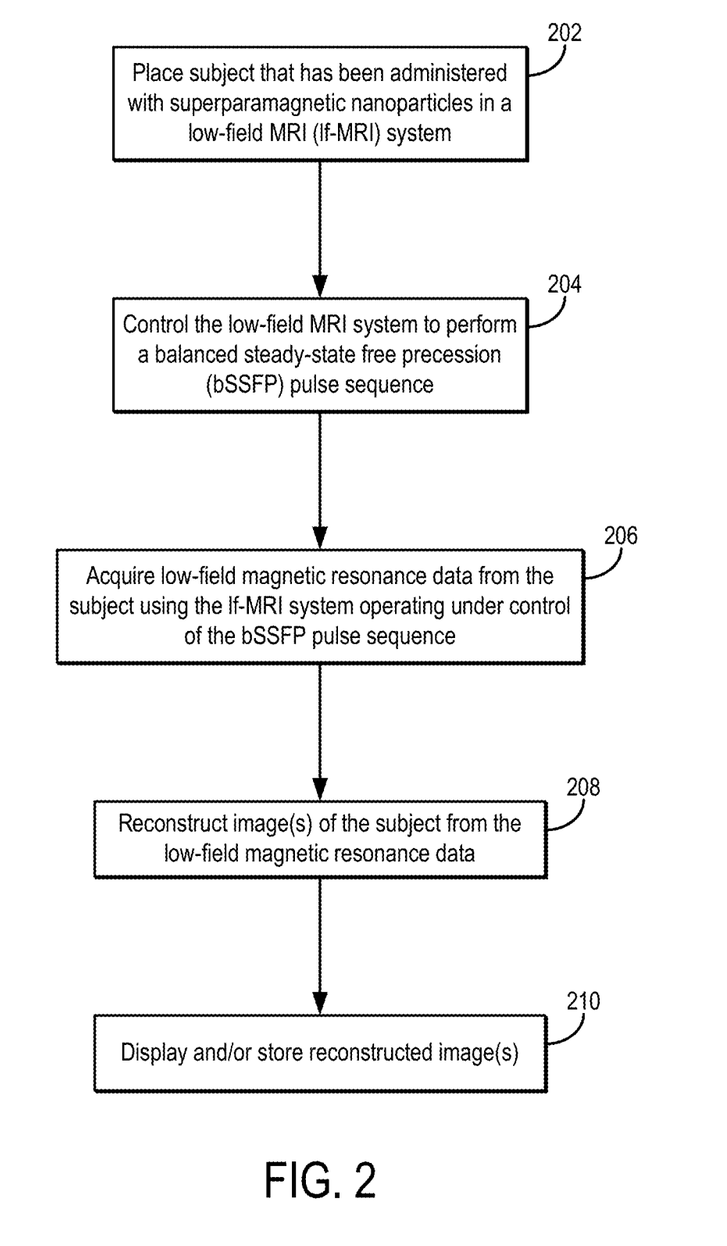
FIG. 2 is a flowchart of non-limiting example steps for reconstructing an image from a subject that has been administered superparamagnetic nanoparticles.

Referring to FIG. 2, a flowchart of non-limiting example steps is shown for generating an image of a subject that has been administered superparamagnetic nanoparticles. The method includes positioning the subject, who has been administered superparamagnetic nanoparticles, within the magnetic field generated by a low-field MRI system, as indicated at step 202. The superparamagnetic nanoparticles may have been previously administered to the subject in the form of an injectable contrast agent or may be provided to the subject in real-time during the scan, such as via a pulsed or continuous intravenous administration.

In a non-limiting example, the superparamagnetic nanoparticles can be superparamagnetic iron oxide nanoparticles ("SPIONs"). SPIONs may be imaged with lf-MRI or used as ULF contrast agents that give sensitive contrast with time-efficient imaging techniques. Superparamagnetic nanoparticles may be selected for their high magnetization at magnetic field strengths at or less than 0.2T, at or less than 6.5 mT, or at or less than other low-field or ultra-low-field strengths. As one example, such superparamagnetic nanoparticles may include high-susceptibility SPIONs (HS-SPIONs), but any other superparamagnetic nanoparticles with suitable magnetization characteristics as the desired low or ultra-low field strengths may be used, such as ferumoxytol SPIONs.

In some implementations, the superparamagnetic nanoparticles can be developed into a targeted contrast agent via surface functionalization with antigens, or the like.

In some configurations, the superparamagnetic nanoparticles can be adapted for use as a blood pool contrast agent for use in clinical applications such as imaging the brain. For instance, the nanoparticle composition can be adapted to limit sequestration of superparamagnetic nanoparticles by the liver. Non-limiting examples to limit liver sequestration include the use of superparamagnetic nanoparticles 100 nm or smaller in size, functionalizing the nanoparticle surface with a biocompatible polymer such as polyethylene glycol ("PEG"), or both.

The MRI system, which may be an lf-MRI system, ULF-MRI system, or the like, may be controlled to perform a bSSFP pulse sequence at step 204. The MRI system may be controlled such as by using a user interface, or by selecting a pre-determined pulse sequence or imaging process, or the like. In some configurations, step 204 includes controlling at least one gradient coil system configured to produce magnetic fields to encode nuclear magnetic resonance signals emitted from the subject and at least one radio-frequency ("RF") coil system configured to produce excitation pulses to perform a bSSFP pulse sequence, or other similar time-efficient pulse sequence capable of susceptibility imaging, to acquire magnetic resonance data from the subject. Controlling the MRI system may include adjusting one or more parameters of the pulse sequence in order to generate a positive contrast from the superparamagnetic nanoparticles that have been administered to the subject.

For instance, controlling the MRI system may include adjusting the RF tip angle, $\alpha$, used for RF excitation pulses in the pulse sequence, the frequency offset, $f_{offset}$, between the Larmor frequency and RF pulse frequency, or both. As a non-limiting example, shifting the RF drive frequency by (½TR) quenches the magnetic resonance signal from on-resonance spins while maintaining the magnetic resonance signal from spins off resonance.

In still other instances, controlling the MRI system may include adjusting other parameters of the pulse sequence, such as the repetition time ("TR") to promote or otherwise induce a positive contrast from the superparamagnetic nanoparticles. For example, increasing TR leads to smaller magnetization plateaus and significant changes in magnetic resonance signal for $^1H$ spins with smaller frequency offsets.

The imaging methods described in the present disclosure may cause the acquired magnetic resonance data to include negative contrast induced by the high $R_2$ relaxivity of SPIONs at low or ultra-low fields. In some other configurations, the pulse sequence can be controlled to cause the magnetic resonance data to include positive contrast, which may be preferred by clinicians, since negative contrast signals can be confounded by the presence of air or hemorrhage. Thus, as described, in some configurations a susceptibility-based positive contrast technique for MRI is provided. This positive imaging contrast is directly enabled by the high magnetization of SPIONs or other suitable superparamagnetic nanoparticles. The basis of positive contrast may be a shift in Larmor resonance frequency of $^1H$ spins induced by the local magnetic field of magnetized SPIONs, or other suitable superparamagnetic nanoparticles. In a non-limiting example bSSFP acquisition, the MRI signal magnitude may be directly proportional to the steady-state transverse magnetization of $^1H$ spins, which in turn depends strongly on the RF tip angle used as well as the offset, $f_{offset}$, between Larmor frequency of the hydrogen proton ($^1H$) spins and RF pulse frequency.

In some configurations, the bSSFP scan may be acquired using an RF excitation pulse with a tip angle at, or close to, an RF tip angle of $\alpha=90$ degrees. In these instances, the imaged $^1H$ spins lie on the plateau around $f_{offset}=0$ Hz and undesired "banding" artifacts due to shifts in Larmor resonance frequency, typically caused by magnetic field inhomogeneities, are suppressed. The high absolute magnetic field homogeneity of low-field magnets make the lf-MRI and/or ULF-MRI regime inherently robust to these banding artifacts, allowing smaller bSSFP tip angles (such as $\alpha=20$ degrees) that selectively boost the MRI signal from $^1H$ spins as they are shifted off resonance by the bulk susceptibility effects of SPIONs.

Referring still to FIG. 2, magnetic resonance data, which may be low-field magnetic resonance data, may be acquired from the subject at step 206 using the MRI system being operated in accordance with the bSSFP pulse sequence. The acquired data may include raw k-space data, which may be acquired from a region-of-interest ("ROI") in the subject, such as a tissue or organ of the subject, a target-of-interest or tumor within the subject, a region containing or adjacent to the superparamagnetic nanoparticles, and the like. The acquired data may also include contrast information between the superparamagnetic nanoparticles and the tissue or organ of the subject, or the target-of-interest/tumor.

An image of the subject may be reconstructed from the acquired low-field magnetic resonance data, as indicated at step 208. Reconstructing an image of the subject, which has been administered a dose of superparamagnetic nanoparticles, may include reconstructing an image in which the superparamagnetic nanoparticles generate a negative image contrast (i.e., the superparamagnetic nanoparticles appear dark in the image) induced by the spin-spin ($R_2$) relaxivity of the superparamagnetic nanoparticles in the low-field B0. Additionally or alternatively, an image may be reconstructed in which the superparamagnetic nanoparticles generate a positive image contrast (i.e., the superparamagnetic nanoparticles appear bright in the image) created by susceptibility weighting of the low-field magnetic resonance data. As described above, the image contrast can be controlled by adjusting one or more parameters of the bSSFP pulse sequence used to control the operation of the MRI system. In some embodiments, the magnetic resonance data acquired in step 206 can include a first set of magnetic resonance data acquired such that the superparamagnetic nanoparticles have a negative contrast and a second set of magnetic resonance data acquired such that the superparamagnetic nanoparticles have a positive contrast. In this way, the reconstructed images can include one or more images in which the superparamagnetic nanoparticles are depicted with a negative contrast and one or more images in which the superparamagnetic nanoparticles are depicted with a positive contrast.

The reconstructed image(s) can then be displayed to a user, or stored for later use, as indicated at step 210. For example, the images can be displayed to a user to provide visualization of a region or target of interest in real-time, or near real-time, or can be stored for subsequent processing and/or later viewing by a clinician. As an example, difference images can be computed between pre-contrast images (i.e., images acquired before the superparamagnetic nanoparticles have been administered to the subject) and post-contrast images (i.e., images acquired after the superparamagnetic nanoparticles have been administered to the subject). Additionally or alternatively, difference images can also be computed between two images acquired with different parameter settings. For instance, a difference image can be computed between a first image acquired using a first set of pulse sequence parameters that result in a first image contrast from the superparamagnetic nanoparticles, and a second image acquired using a second set of pulse sequence parameters that result in a second image contrast from the superparamagnetic nanoparticles. As a non-limiting example, the first image contrast may correspond to a negative image contrast and the second image contrast may correspond to a positive image contrast, or the first and second image contrasts may both correspond to positive contrasts in which the superparamagnetic nanoparticles are depicted with different levels of brightness.

As another example, the reconstructed images can be processed to quantify or otherwise estimate one or more physical parameters (e.g., magnetization, concentration) of the superparamagnetic nanoparticles present in a region-of-interest within the subject. For instance, to determine the magnetization, of contrast agents at low or ultra-low field (e.g., 6.5 mT), bSSFP MRI images with banding artifacts caused by contrast agent magnetization may be acquired. The measured data may be fit with simulated images calculated from equations for magnetization of contrast agent vials and the bSSFP MRI signal equation. To simulate image artifacts a model may be used, which may be an analytical calculation of the magnetic field produced by an infinitely long vial of contrast agent placed transverse to a static, x-directed, magnetic field (B0). Defining B0 in the x-direction is unconventional in MRI, but appropriate in these calculations as it means the z-direction is parallel to the axis of the contrast agent vial and conventional cylindrical coordinates may be used.

In a non-limiting example, for a water region of a phantom, the change in magnetic field ($\Delta B_x$) induced by magnetization of the contrast agent is given by:

$$\Delta B_x = \mu_0 (1 + \chi_3) \frac{D_3}{r^2} \cos 2\phi \qquad (3)$$

where $D_3$ is a constant. For gadolinium-based contrast agents, $D_3$ can be given by, $$D_3 = \frac{H_0 r_2^2 (r_2^2 (2 + \chi_1 + \chi_2)(\chi_2 - \chi_3) + r_1^2((\chi_1 - \chi_2)(2 + \chi_2 + \chi_3)))}{r_1^2 (\chi_1 - \chi_2)(\chi_2 - \chi_3) + r_2^2 (2 + \chi_1 + \chi_2)(2 + \chi_2 + \chi_3)} \qquad (4)$$

and for iron oxide-based contrast agents, $D_3$ can be given by, $$D_3 = -\frac{r_2^2 (2 M_s r_1^2 (1 + \chi_2) - H_0 (-r_2^2 (2 + \chi_2)(\chi_2 - \chi_3) + r_1^2 \chi_2 (2 + \chi_2 + \chi_3)))}{r_1^2 \chi_2 (\chi_2 - \chi_3) - r_2^2 (2 + \chi_2)(2 + \chi_2 + \chi_3)} \qquad (5)$$

In these equations, $\chi_1$ is the magnetic susceptibility of the region containing contrast agent ($0 < r < r_1$), $\chi_2$ is the susceptibility of the glass vial ($r_1 < r < r_2$) and $\chi_3$ the susceptibility of water ($r > r_2$). The variables r and $\phi$ are cylindrical coordinates defined relative to the center of the phantom and the $B_0$ field direction. $r_1$ and $r_2$ are the inner and outer radii of the contrast agent vial. $H_0$ is the applied magnetic field strength and $M_s$ is the contrast agent magnetization. $\mu_0$ is the permeability of free space. From Eqn. (3), the shift in Larmor resonance frequency can be calculated as $\Delta f_L = \gamma_H \Delta B_x$. This frequency shift may be used in conjunction with the TR and tip angle, $\alpha$, to produce an analytical bSSFP image using the bSSFP signal. As a magnetic field strength of 6.5 mT, the ratio of T1/T2=1, resulting in the following expression for transverse magnetization:

$$M_{xy}(\Delta f, \alpha) = M_0 \frac{\sin\alpha \sqrt{1 + 1\cos(2\pi \cdot \Delta f \cdot T_R)}}{2(T_1/T_2)(1 - \cos\alpha) + (1 + \cos(2\pi \cdot \Delta f \cdot T_R))(1 + \cos\alpha)}. \qquad (6)$$

All values except the magnetization of the contrast agent (e.g., $M = M_s(H/|H|)$) for superparamagnetic nanoparticles and $M = \chi_1 H$ for Gd) are known for phantom images. Experimental images may be fit by analytical images via interpolation of simulated data onto an equivalent resolution grid for different values of $M_s$. In a non-limiting example, the magnetization value that gives the highest 2D correlation coefficient between water regions in experimental and simulated data may be selected as the best fit. Magnetization error bars may be calculated as the change in magnetization required for a specified drop, such as a 10% drop, in 2D correlation coefficient.

In some configurations, the longitudinal relaxivity ($R_1$) and the transverse relaxivity ($R_2$) of contrast agents may be determined by fitting $T_1$ (inversion recovery) and $T_2$ (Hahn echo) measurements, respectively, to the concentration dependent relaxivity equation:

$$\frac{1}{T_{1,2}} = \frac{1}{T_{1,2}^0} + R_{1,2}[CA]; \qquad (7)$$

where $T_{1,2}$ is the $^1$H relaxation time of the solution with contrast agent, $T^0_{1,2}$ is the $^1$H relaxation time in the absence of contrast agent, $R_{1,2}$ is the relaxivity coefficient, and [CA] is the concentration of contrast agent. Table 1 below includes non-limiting example $R_{1,2}$ values for conventional field strengths.

TABLE 1

Non-limiting example relaxivity coefficients

| | Magnetic Field Strength (T) | |
| --- | --- | --- |
| | 3 | 7 |
| $r_1$ (mM$^{-1}$s$^{-1}$) | 0.86 ± 0.13 | 0.44 ± 0.13 |
| $r_2$ (mM$^{-1}$s$^{-1}$) | 179 ± 12 | 585 ± 9 |

Table 1 shows the relaxivity values of carboxylated, HS-SPIONs measured in preclinical 3 T and 7 T MRI scanners. T1 and T2 values were obtained by fitting phantom imaging data acquired with a fast spin echo ("FSE") sequence to standard magnetization recovery ($T_1$) and magnetization decay ($T_2$) models for various TR/TE.

Superparamagnetism, which in some configurations is a result of the exchange interaction in iron, leads to full alignment of the magnetic moments of iron atoms within SPIONs, such that each nanoparticle behaves as one large magnetic moment on the order of ten thousand Bohr magnetons in magnitude. These magnetic moments near fully align with modest external magnetic fields, giving SPION contrast agents magnetizations and $^1$H relaxivities that are orders of magnitude larger at ULF than paramagnetic contrast agents, such as Gd-DTPA, that rely on the relatively weak Zeeman interaction for magnetization alignment. By leveraging these high magnetizations and relaxivities, high-sensitivity, high-contrast imaging using lf-MRI or at ULF may be achieved.

Figure 3A:
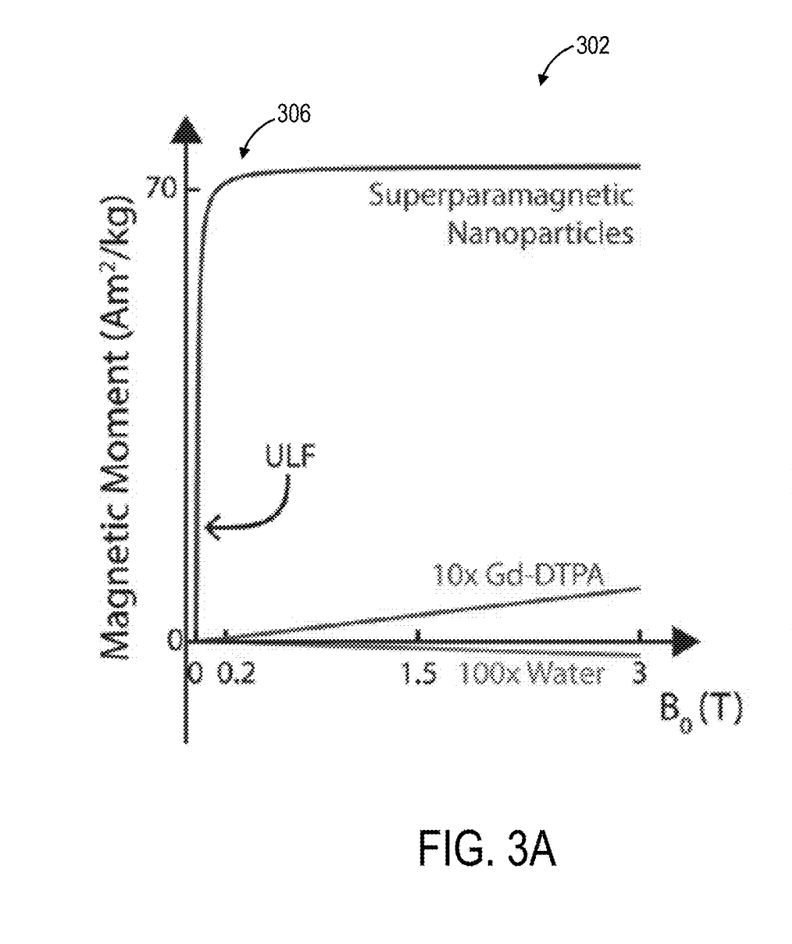
FIG. 3A is a graph of non-limiting example magnetic moments for superparamagnetic nanoparticles.
Figure 3B:
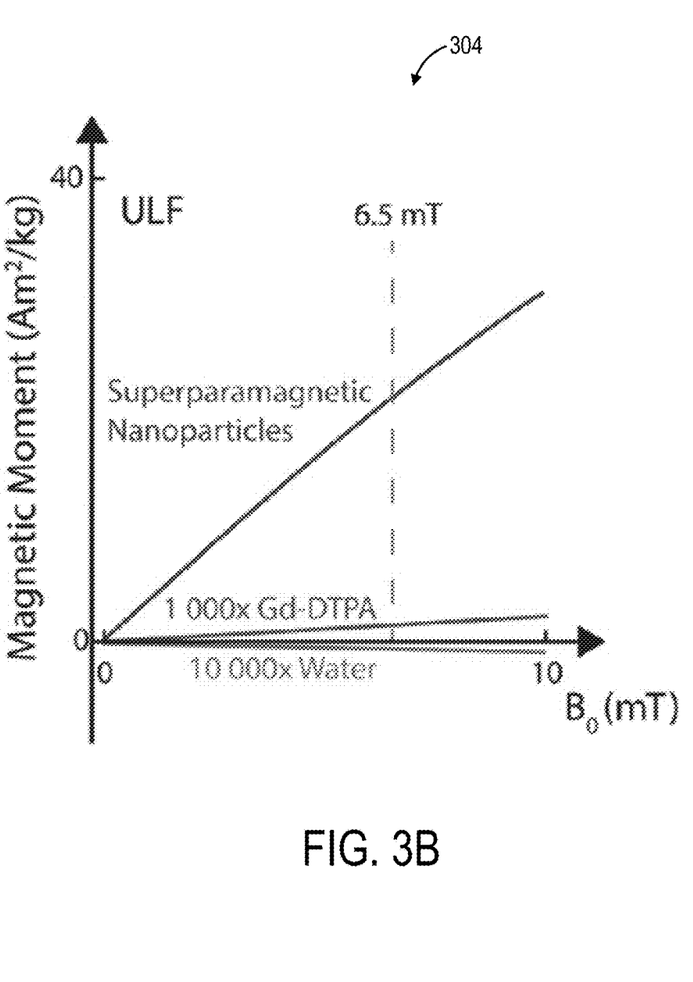
FIG. 3B is another graph of non-limiting example magnetic moments for superparamagnetic nanoparticles at a different scale.

Referring to FIGS. 3A and 3B, graphs 300 and 302 of non-limiting example magnetic moments for superparamagnetic nanoparticles are shown for different scales. Magnetization of 25 nm SPIONs, gadolinium contrast agent (Gd-DTPA/Magnevist) and water are shown as a function of magnetic field strength (B0). For FIG. 3B, magnetization is shown as a non-limiting example, a function of magnetic field strength (B0) in an ultra-low field (<10 mT) regime for the materials shown in FIG. 3A. Superparamagnetic materials, such as SPIONs, are highly magnetized even at <10 mT. Paramagnetic materials, such as contrast agents based on gadolinium, and body tissues (which typically have anemia treatments) and Magnevist (Gd-DTPA) are shown. Core sizes and hydrodynamic diameter (HD) are reproduced from references or taken from manufacturer datasheets. Magnetic moment (M) values at 6.5 mT were calculated per kg of Fe/Gd from susceptibility imaging.

| Contrast Agent | Core (nm) | HD (nm) | M ($A \cdot m^2$/kg Fe/Gd) | $r_1$ ($mM^{-1}s^{-1}$) | $r_2$ ($mM^{-1}s^{-1}$) | $r_2/r_1$ |
|---|---|---|---|---|---|---|
| HS-COOH | 24.2 | 43.4 | 38.5 ± 1.5 | 320 ± 15 | 365 ± 43 | 1.14 ± 0.13 |
| HS-PEG | 24.2 | 92.9 | 33.3 ± 1.9 | 261 ± 20 | 329 ± 45 | 1.26 ± 0.17 |
| Ferumoxytol | 3.3 | 30 | 4 ± 0.6 | 31 ± 1 | 31 ± 4 | 1.00 ± 0.13 |
| Gd-DTPA | $Gd^{3+}$ | 1.8 | 0.010 ± 0.002 | 3.4 ± 0.1 | 11 ± 1 | 3.24 ± 0.29 | diamagnetic susceptibilities close to water) have absolute magnetizations that increase linearly with field strength. Curves reflect the magnetic moment per kilogram of compound. As described herein, the nanoparticle may be selected based on the low field strength that will be used for imaging. In one non-limiting example, it may be desirable to select a nanoparticle size and composition to align with an "elbow" 306 the plot at the imaging field strength illustrated in FIG. 3A, or similar plots for different nanoparticles. Generally smaller nanoparticles will increase the field strength at which the "elbow" occurs, whereas bigger nanoparticles will decrease the field strength.

In some configurations, superparamagnetic nanoparticles include Magnetite ($Fe_3O_4$) SPIONs. In a non-limiting example, the SPIONs include highly susceptible (HS) SPIONs that have 25 nm iron oxide cores functionalized with carboxylic acid (COOH) or polyethylene glycol (PEG). The behavior of these HS-SPIONs may be compared to gadopentetic acid (Gd-DTPA), a widely used T1 contrast agent in clinical MRI, and ferumoxytol SPIONs (approved by the FDA for anemia treatments).

The HS-SPIONs have measured magnetizations at <10 mT over 3000 times larger than conventional Gd-DTPA contrast agents. As the SPION magnetic moments fluctuate, they couple to nearby $^1H$ nuclei, causing a shortening of spin relaxation times. HS-SPIONs have spin-lattice ($R_1$) and spin-spin ($R_2$) relaxivity values at <10 mT in excess of 300 $mM^{-1}s^{-1}$, nearly two orders of magnitude larger than that for the Gd-DTPA. Relaxivity values for the HS-SPIONs are approximately 10 times that observed for ferumoxytol SPIONs, predominantly due to the higher magnetization reached in the larger iron oxide cores of the HS-SPIONs.

In Tesla-strength magnetic fields, SPIONs can be advantageously utilized for T2-weighted imaging due to large $R_2/R_1$ ratios. In some configurations, the HS-SPIONs may have $R_2/R_1$=208 at 3 T. In some configurations, $R_2/R_1$ ratios (a measure of $T_1$ contrast power) for all contrast agents may be close to unity at 6.5 mT. The $R_1$ values observed at 6.5 mT for SPIONs may be significantly higher than seen at clinical field strengths, which indicates the potential of SPIONs for $T_1$-weighted imaging at low or ultra-low fields, especially when compared to gadolinium-based CAs. PEGylation of HS-SPIONs may have a limited impact on relaxivity despite causing a significant increase in hydrodynamic diameter (HD), indicating that long range effects may dominate $^1H$ relaxation.

Table 2 below shows size, magnetization, and contrast power of different contrast agents at 6.5 mT. Data for 25 nm carboxylated iron oxide nanoparticles (HS-COOH), 25 nm PEGylated iron oxide nanoparticles (HS-PEG), Feraheme SPIONs (ferumoxytol, FDA-approved for iron-deficiency In a non-limiting example, when using 6.5 mT lf-MRI, a 25 nm HS-SPIONs was used because the characteristic magnetic field required to magnetized them was <10 mT. At smaller field strengths (e.g., 1 mT), likely larger SPIONs are desired for the susceptibility imaging. At higher field strengths, smaller SPIONs can be used. In some configurations, the size of superparamagnetic nanoparticles may be chosen to optimize magnetization at the imaging magnetic field strength.

In some configurations, a bSSFP pulse sequence may be used for imaging the superparamagnetic nanoparticles, as described above. bSSFP sequences may satisfy the high efficiency demands of ULF imaging and may be sensitive to magnetic susceptibility changes, enabling the location of highly magnetized superparamagnetic nanoparticles to be imaged. Such nanoparticles being used as contrast agents may also serve to alleviate the increasing concerns over the neuroaccumulation of gadolinium contrast agents. Due to the nonlinearity of superparamagnetism, superparamagnetic nanoparticles may be used to reach a determined level of their field-saturated magnetization at ultra-low-field strengths (e.g., 6.5 mT), enabling the use of susceptibility-based contrast techniques at ULF. Due to the negligible magnetizations induced in human tissues at low magnetic field, susceptibility-weighted imaging has not been previously adopted for use in ULF MRI. The accuracy of superparamagnetic nanoparticles-based diagnosis may be aided by the suppression of background susceptibility artifacts using lf-MRI or at ULF—a challenge that has hindered the widespread use of superparamagnetic nanoparticles at high fields.

Despite the 460-fold reduction in field strength for a ULF system from 3 T, scans using superparamagnetic nanoparticles may be possible over similar clinical timeframes. Additionally, opportunities exist to increase SNR and CNR. A tip-angle based approach may be used, and variations in TR and transmit frequency may also be used to selectively probe regions of superparamagnetic nanoparticles with additional positive contrast at lower concentrations. Calculating difference images via post-processing techniques may also be used in identifying regions of significant superparamagnetic nanoparticle uptake.

Positive contrast methods may be used to aid in identification of superparamagnetic nanoparticles in lf-MRI or ULF images. Positive contrast methods may include the use of a bSSFP pulse sequence. The contrast techniques at 6.5 mT can also be extended to low-field MRI scanners based on permanent magnets. Iron oxide nanoparticle size may also be customized to maximize magnetization and $^1H$ relaxivity at the desired field strength.

In some configurations, increasing SNR and CNR using lf-MRI or at ULF includes the use of sensitive superconducting quantum interference devices ("SQUIDs") or hyperpolarization techniques that can boost nuclear spin polarizations by orders of magnitude. Challenges associated with a time-consuming pre-polarization step and concerns over the toxicity of free-radical-based hyperpolarization agents, respectively, may be addressed in accordance with the present disclosure. The contrast mechanisms may also be useful for the integration of MRI with new theranostic modalities including magnetic particle imaging ("MPI") and superparamagnetic relaxometry that utilize the unique properties of superparamagnetic nanoparticles using low or ultra-low magnetic field strengths. Such new modalities, which may be highly advantageous for early detection and diagnosis of diseases such as cancer, may use a complementary system for anatomical imaging such as a CT or lf-MRI scanner to address any incompatibilities with the high magnetic fields of clinical MRI scanners.

In some configurations, a sensitive contrast agent is provided that may be applicable to other implementations of portable and low-field MRI. Given their unique low-field properties, tailored superparamagnetic nanoparticles may be used as the CA of choice for lf-MRI.

SPIONs at <10 mT have high relaxivity and may be used as a high-sensitivity in vivo contrast agent imaging in a 6.5 mT MRI scanner. An in vivo experiment was performed on a $^1$H anatomy scan of an anesthetized Wistar rat using bSSFP MRI. At the ultra-low magnetic field strength of 6.5 mT, SNRs of 24.4±2.3 and 11.8±1.3 were measured in adipose and liver tissues, respectively, following a short scan (duration of 12.5 minutes). The bSSFP acquisition enabled the sensitivity of the imaging at low or ultra-low field, after which the resulting images are weighted by the ratio of $T_2/T_1$. As this ratio is nearly unity at this low or ultra-low field, the images displayed for a user may be essentially proton-density weighted and as a result have very little observable contrast between organs.

Following anatomical imaging, PEGylated HS-SPIONs were injected into the tail vein at a dose of 5 mg/kg. Significant negative contrast was observed in highly perfused organs such as the kidneys and liver due to the presence of SPIONs in images acquired 30 minutes after injection. In particular, the MRI signal from the liver was almost entirely eliminated, giving a CNR of 6.3 when signal intensity is compared to pre-injection imaging.

Having demonstrated in vivo contrast with SPIONs and bSSFP MRI at low or ultra-low fields, the sensitivity of the underlying contrast mechanism was examined. For fixed $T_R/T_E$, the negative bSSFP contrast arises when the presence of CA causes $T_2$ to become smaller than $T_E$ (25 ms in this setup). From the relaxivity data in Table 2 this concentration threshold is reached for HS-SPIONs at 100 μM with the imaging parameters used in the non-limiting example. The 100 μM concentration threshold was comfortably exceeded by the post-injection concentration of SPIONs in the bloodstream (calculated to be 1 mM assuming a 25 mL rat blood volume). The in vivo SPION dose used equates to 90 μM Fe per kg of body weight, which is approximately three times lower than clinical doses used in iron replacement therapies. With 12.5 min imaging acquisition time, this makes the imaging over 150 times more sensitive, in terms of minimum mass concentration threshold, than nanoparticle imaging modalities based on hyperpolarization. Further, these in vivo results were obtained with voxel sizes nearly 100 times smaller and an acquisition 8 times faster than previous demonstrations of a T1-weighted approach to SPION imaging in phantoms at low or ultra-low fields. SPIONs may remain visible in the bloodstream until the conclusion of imaging (approximately 2 hours post-injection in the non-limiting example), as evidenced by persistent negative contrast in the aorta and vena cava.

To test the potential of gadolinium as a contrast agent at low or ultra-low fields, the experiment was repeated at the typical maximum clinical dose of Gd-DTPA (0.2 mL/kg or 100 μM/kg). Little to no contrast was seen due to the Gd-DTPA injection in bSSFP imaging, as would be expected from the comparatively low relaxivity of Gd-DTPA. Obtaining the contrast threshold of $T_2<T_E$ in this experiment would require a bloodstream concentration of 4 mM Gd-DTPA, which is higher than can be achieved at the maximum clinical dose.

Figure 4:
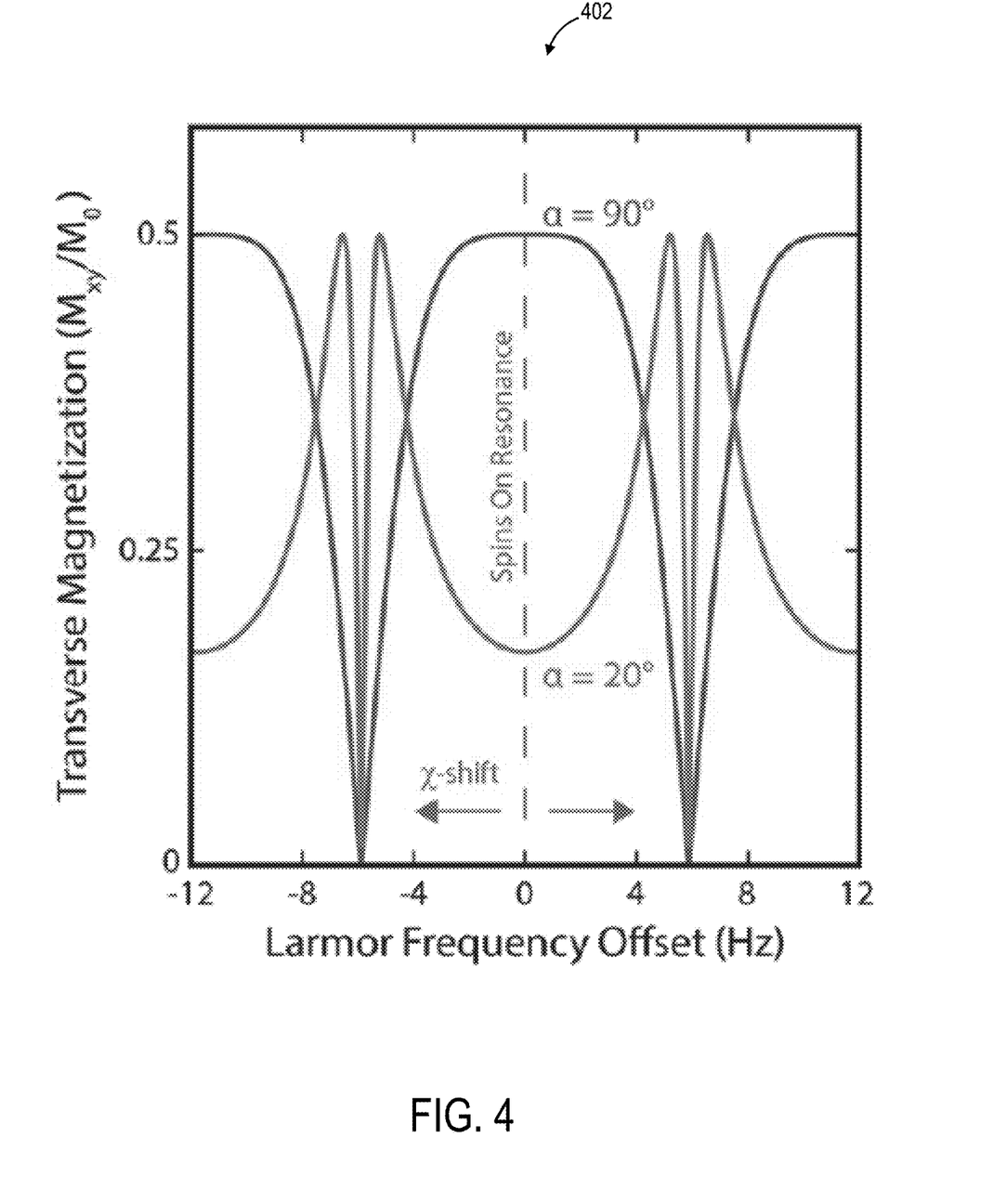
FIG. 4 is a graph of non-limiting example transverse magnetization of spins during bSSFP imaging.

Referring to FIG. 4, a graph 402 of non-limiting example transverse magnetization of spins during bSSFP imaging is shown. MRI signal magnitude is proportional to the transverse magnetization ($M_{xy}$) of $^1$H nuclear spins, which is shown as a function of frequency offset (the difference between RF pulse frequency and Larmor precession frequency). Spins not in the presence of SPIONs have zero Larmor frequency offset. As SPION concentration increases, nearby spins experience a susceptibility ($\chi$) shift in Larmor frequency. Curves for RF pulse tip angles of α=20 degrees and α=90 degrees are shown. The transverse magnetization is normalized by the fully relaxed longitudinal magnetization ($M_0$). $T_R$=85 ms and $T_1/T_2$=1 in this model.

In a non-limiting example of positive contrast boost that results from off-resonance spins, a phantom containing HS-SPIONs was suspended in water. When α=90 degrees was used, water surrounding the vial of SPIONs displayed dark bands at $^1$H frequency shifts of $±½T_R$ (±6 Hz) overlaid on a uniform background signal intensity. Imaging with a low α of 20 degrees revealed the vial with positive contrast as signal boosting occurs adjacent to these same dark bands. By fitting imaging data to the bSSFP signal model and approximating the vial of SPIONs as a long cylinder, the SPION magnetization (values shown in Table 1) as well as the spatial, susceptibility-based shift in 1H frequency were determined.

The concentration sensitivity of the method may be quantified by imaging a HS-SPION phantom. Negative contrast within the SPION solution may be observed due to T2-shortening effects, which may begin to manifest at the same 0.1 mM concentration threshold at which positive contrast in adjacent structures becomes visible in a α=20 degree scan. The concentration threshold for imaging ferumoxytol SPIONs with negative and positive contrast (~1 mM) is higher than for HS-SPIONs, as would be expected from their lower relaxivity and magnetization at low or ultra-low fields. Repeating the two tip-angle imaging with a phantom containing Gd-DTPA, negative, relaxivity-based contrast was present at a relatively high concentration of 10 mM. No positive contrast was observed from Gd-DTPA in the α=20 degree scan, as the magnetization of the paramagnetic compound is too low. Positive contrast can be observed in an α=20 degree scan of Gd-DTPA by increasing the concentration to a clinically unfeasible 500 mM.

As phantoms typically enhance MRI contrast, non-limiting example positive-contrast imaging was performed with SPIONs at low or ultra-low fields in a healthy rat model. Immediately after anesthetization, pre-injection anatomy scans were acquired with α=90 degrees and α=20 degrees. Comparing pre-injection scans, time-weighted SNR of adipose tissue in the 20-degree scan was a factor of 2.9 lower than in the 90-degree scan, which is consistent with the reduction in transverse magnetization for on-resonance spins.

Contrast between tissues in 90-degree and 20-degree scans is qualitatively identical, as all spins are on-resonance and transverse magnetization is suppressed uniformly. Following anatomy scans, HS-SPIONs functionalized with COOH were administered at 5 mg/kg and 30 minutes allowed for biodistribution of SPIONs. In post-injection images, clear differences between 90-degree and 20-degree acquisitions are immediately apparent. While the 90-degree images show negative contrast in the liver and kidneys, the 20-degree images show positive contrast around regions of SPION uptake due to signal boosting of off-resonance spins. SNR increased by 1.7 in tissue posterior to the liver when compared to the 20-degree pre-injection scan. Tissue anterior to the liver experienced a post-injection resonance shift, as it also lied along the dipole axis of magnetized SPIONs. This anterior region appeared dark in the post-injection 20-degree scan, likely due to significant concentrations of SPIONs causing T2-shortening in this highly vascularized tissue. MRI signals from, and around, tissues that have minimal SPION uptake, such as adipose tissue, was again suppressed when imaged with α=20 degrees. Unlike the PEGylated SPIONs, the HS-COOH SPIONs were not visible in the vena cava at the conclusion of imaging. This difference was likely due to the rapid removal from the bloodstream of nanoparticles with negative zeta potential, such as carboxylated SPIONs, by the immune system.

Figure 5A:
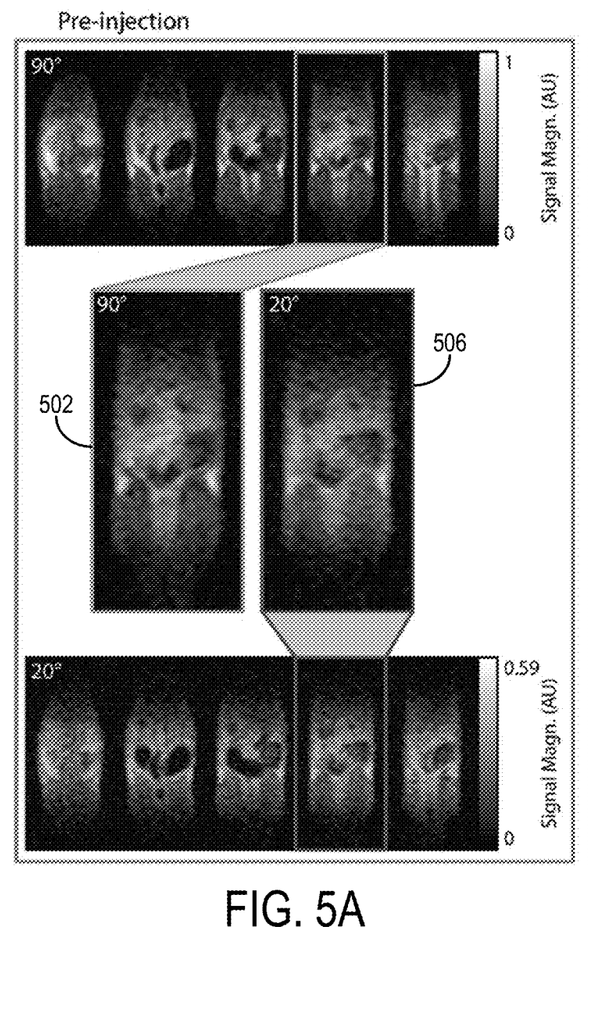
FIGS. 5A and 5B illustrate example images obtained before (FIG. 5A) and after (FIG. 5B) superparamagnetic nanoparticles were administered to a rat subject and using 90 degree and 20 degree RF tip angles.
Figure 5B:
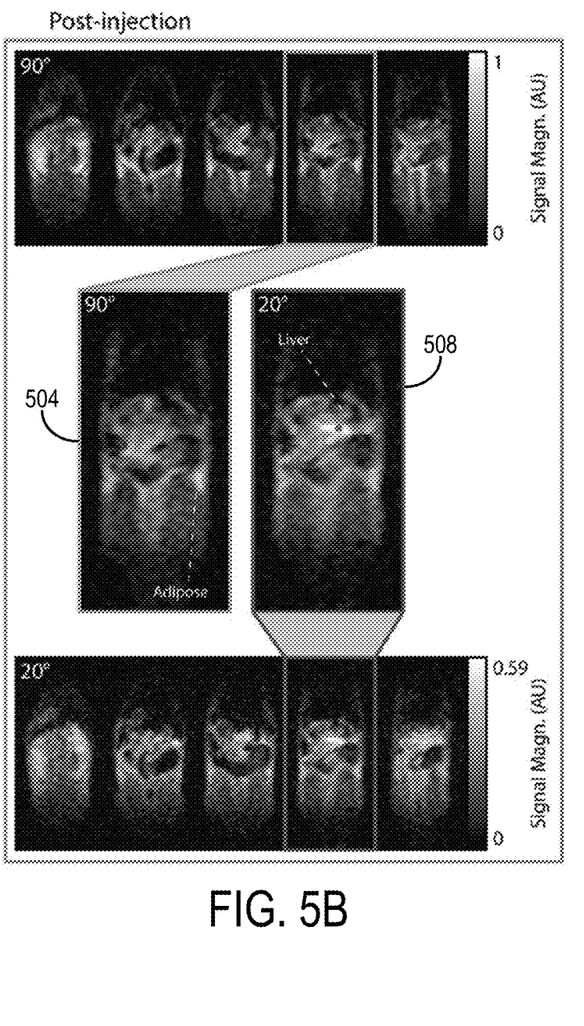

FIGS. 5A and 5B illustrate switchable susceptibility-based SPION contrast. FIG. 5A illustrates images of rat anatomy before contrast agent injection acquired with bSSFP tip angles of α=90 degrees (top) and α=20 degrees (bottom). FIG. 5B illustrates MRI scans taken 30 minutes after a tail-vein injection of HS-COOH SPIONs at 5 mg/kg with α=90 degrees (top) and α=20 degrees (bottom). The five central slices of 11-slice datasets are shown for each acquisition. Expanded images of individual slices from α=90 degrees datasets 502, 504 and α=20 degrees datasets 506, 508 are shown. Field of view in each slice is 155 mm×73 mm.

The present disclosure has described one or more preferred embodiments, and it should be appreciated that many equivalents, alternatives, variations, and modifications, aside from those expressly stated, are possible and within the scope of the invention.

The invention claimed is:

1. A low-field magnetic resonance imaging (lf-MRI) system comprising:
    at least one magnet configured to produce a low-field B0 magnetic field;
    at least one gradient coil system configured to produce magnetic fields to encode nuclear magnetic resonance signals emitted from a subject;
    at least one radio-frequency (RF) coil system configured to produce excitation pulses; and
    at least one computer system configured to:
        control the gradient coil system and the RF coil system to perform a balanced steady-state free precession (bSSFP) pulse sequence to acquire lf-MRI data from a subject having received a dose of superparamagnetic nanoparticles; and
        reconstruct an image of the subject, wherein the image has at least one of a negative contrast induced by spin-spin (R2) relaxivity of the superparamagnetic nanoparticles in the low-field B0 or a positive contrast created by susceptibility weighting of the lf-MRI data.

2. The lf-MRI system of claim 1, wherein the image is a T1-weighted image.

3. The lf-MRI system of claim 1, wherein the positive contrast is created by a shift in Larmor resonance frequency of $^1H$ spins induced by a local magnetic field of the superparamagnetic nanoparticles.

4. The lf-MRI system of claim 1, wherein the computer system is further configured to control the gradient coil system and the RF coil system to perform the bSSFP pulse sequence to include variations in repetition time (TR) or transmit frequency to create the positive contrast.

5. The lf-MRI system of claim 1, wherein the computer system is further configured to use a tip angle of less than 90 degrees with the bSSFP pulse sequence to selectively boost the signal from $^1H$ spins shifted off resonance by bulk susceptibility effects of the superparamagnetic nanoparticles.

6. The lf-MRI system of claim 1, wherein the computer system is further configured to use superconducting quantum interference devices (SQUIDs) or hyperpolarization techniques to boost nuclear spin polarizations and increase at least one of signal-to-noise ratio or contrast-to-noise ratio of the lf-MRI data.

7. The lf-MRI system of claim 1, wherein the at least one magnet is configured to produce the low-field B0 magnetic field with a magnetic field strength less than 1.0 Tesla.

8. The lf-MRI system of claim 7, wherein the at least one magnet is configured to produce the low-field B0 magnetic field with a magnetic field strength less than 0.2 Tesla.

9. The lf-MRI system of claim 8, wherein the at least one magnet is configured to produce the low-field B0 magnetic field with a magnetic field strength of 6.5 mT.

10. A method for magnetic resonance imaging (MRI), comprising:
    acquiring magnetic resonance data from a subject that has received a dose of superparamagnetic nanoparticles using an MRI system, wherein acquiring the magnetic resonance data includes controlling the MRI system to perform a balanced steady-state free precession (bSSFP) pulse sequence to acquire the magnetic resonance data from the subject, wherein at least one parameter of the bSSFP pulse sequence is adjusted such that the magnetic resonance data depicts one of a negative contrast for the superparamagnetic nanoparticles induced by spin-spin relaxivity ($R_2$) of the superparamagnetic nanoparticles, or a positive contrast for the superparamagnetic nanoparticles induced by susceptibility weighting; and
    reconstructing an image of the subject from the magnetic resonance data, wherein the image depicts the superparamagnetic nanoparticles with the negative contrast or the positive contrast based on the at least one parameter of the bSSFP pulse sequence.

11. The method of claim 10, wherein reconstructing the image includes reconstructing a T1-weighted image.

12. The method of claim 10, further comprising creating the positive contrast by a shift in Larmor resonance frequency of $^1H$ spins induced by local magnetic field of the superparamagnetic nanoparticles.

13. The method of claim 10, wherein adjusting the at least one parameter of the bSSFP pulse sequence comprises varying at least one of a repetition time (TR) or a transmit frequency to create the positive contrast.

14. The method of claim 10, further comprising using a tip angle of less than 90 degrees with the bSSFP pulse sequence to selectively boost magnetic resonance signals from $^1H$ spins shifted off resonance by bulk susceptibility effects of the superparamagnetic nanoparticles.

15. The method of claim 10, further comprising using superconducting quantum interference devices (SQUIDs) or hyperpolarization techniques to boost nuclear spin polarizations and increase at least one of signal-to-noise ratio or contrast-to-noise ratio of the magnetic resonance data.

16. The method of claim 10, further comprising selecting a size of the superparamagnetic nanoparticles based on a B0 magnetic field strength of the MRI system.

17. The method of claim 16, wherein the size of the superparamagnetic nanoparticles is selected to correspond to an elbow transition of a magnetic moment of the superparamagnetic nanoparticles as a function of the B0 magnetic field strength.

18. The method of claim 10, wherein the MRI system has a B0 magnetic field strength less than 1.0 Tesla.

19. The method of claim 18, wherein the MRI system has a B0 magnetic field strength less than 0.3 Tesla.

20. The method of claim 19, wherein the MRI system has a B0 magnetic field strength of 6.5 mT.

21. The method of claim 10, wherein the superparamagnetic nanoparticles comprise superparamagnetic iron oxide nanoparticles (SPIONs).

22. The method of claim 21, wherein the SPIONs comprise high-susceptibility SPIONs.

23. A method for magnetic resonance imaging (MRI) of a subject that has been administered a dose of superparamagnetic nanoparticles, the method comprising:

acquiring susceptibility-weighted magnetic resonance data from a subject that has received a dose of superparamagnetic nanoparticles using an MRI system performing a pulse sequence;

reconstructing an image of the subject from the susceptibility-weighted magnetic resonance data;

wherein at least one of a radio frequency tip angle, a frequency offset, or a repetition time of the pulse sequence is selected such that the superparamagnetic nanoparticles are depicted in the image with a positive contrast, and wherein the pulse sequence is a balanced steady-state free precession (bSSFP) pulse sequence.

24. The method of claim 23, wherein the MRI system has a B0 magnetic field strength less than 0.3 Tesla.

25. The method of claim 24, wherein the MRI system has a B0 magnetic field strength less than 10 mT.

26. The method of claim 25, wherein the MRI system has a B0 magnetic field strength of 6.5 mT.

27. The method of claim 23, wherein at least one of a size or a composition of the superparamagnetic nanoparticles based is selected based on a B0 magnetic field strength of the MRI system.

28. The method of claim 27, wherein the size or composition of the superparamagnetic nanoparticles is selected to correspond to an elbow transition of a magnetic moment of the superparamagnetic nanoparticles as a function of the B0 magnetic field strength of the MRI system.

* * * * *

UNITED STATES PATENT AND TRADEMARK OFFICE
CERTIFICATE OF CORRECTION

PATENT NO. : 11,835,610 B2
APPLICATION NO. : 17/866069
DATED : December 5, 2023
INVENTOR(S) : Matthew S. Rosen et al.

It is certified that error appears in the above-identified patent and that said Letters Patent is hereby corrected as shown below:

In the Specification

Column 11, Line 8, "magnetization, of" should be --magnetization, M of--.

Column 16, Line 31, "$\pm 1/2T_R$" should be --$\pm 1/2TR$--.

Column 16, Line 33, "a" should be --$\alpha$--.

In the Claims

Claim 7, Column 18, Line 24, "B0magnetic" should be --B0 magnetic--.

Signed and Sealed this
Tenth Day of September, 2024

Katherine Kelly Vidal
*Director of the United States Patent and Trademark Office*